(12) United States Patent
Deppermann et al.

(10) Patent No.: US 8,312,672 B2
(45) Date of Patent: *Nov. 20, 2012

(54) METHODS OF SEED BREEDING USING HIGH THROUGHPUT NONDESTRUCTIVE SEED SAMPLING

(75) Inventors: Kevin L. Deppermann, St. Charles, MO (US); Michael W. Petersen, Sauk City, WI (US); David Butruille, Urbandale, IA (US); Stanton Dotson, Chesterfield, MO (US); Sam Eathington, Ames, IA (US); Heather Forbes, St. Charles, MO (US); Bruce Schnicker, Wildwood, MO (US); John Tamulonis, Nevada, IA (US)

(73) Assignee: Monsanto Technology LLC, St. Louis, MO (US)

( * ) Notice: Subject to any disclaimer, the term of this patent is extended or adjusted under 35 U.S.C. 154(b) by 105 days.

This patent is subject to a terminal disclaimer.

(21) Appl. No.: 13/108,762

(22) Filed: May 16, 2011

(65) Prior Publication Data

US 2011/0217700 A1 Sep. 8, 2011

Related U.S. Application Data

(63) Continuation of application No. 12/767,640, filed on Apr. 26, 2010, now Pat. No. 7,941,969, which is a continuation of application No. 11/680,611, filed on Feb. 28, 2007, now Pat. No. 7,703,238, which is a continuation-in-part of application No. 11/213,435, filed on Aug. 26, 2005, now Pat. No. 7,611,842.

(60) Provisional application No. 60/778,828, filed on Mar. 2, 2006, provisional application No. 60/691,100, filed on Jun. 15, 2005, provisional application No. 60/604,604, filed on Aug. 26, 2004.

(51) Int. Cl.
*A01B 79/00* (2006.01)
*A01B 79/02* (2006.01)
*A01C 1/00* (2006.01)
*A01G 1/00* (2006.01)
*A01H 3/00* (2006.01)

(52) U.S. Cl. .................................................. 47/58.1 R
(58) Field of Classification Search .............. 47/58.1 R; 800/278, 295; 435/6; 436/176
See application file for complete search history.

(56) References Cited

U.S. PATENT DOCUMENTS 2,756,903 A 7/1956 Kreidler
(Continued)

FOREIGN PATENT DOCUMENTS

CL 1035-03 5/2003
(Continued)

OTHER PUBLICATIONS

McEntyre et al., "Comparison of Water Absorption Patterns in Two Barley Cultivars, Using Magnetic Resonance Imaging," *Cereal Chem.*, 75(6):792-795 (1998).

(Continued)

*Primary Examiner* — Kent L Bell
(74) *Attorney, Agent, or Firm* — James E. Davis; Joseph A. Schaper; Harness, Dickey & Pierce, P.L.C.

(57) ABSTRACT

The present invention provides for novel methods to facilitate germplasm improvement activities through the use of high throughput, nondestructive sampling of seeds. A method for analyzing a population of haploid seeds generally includes providing a population of seeds comprising haploid seeds, removing tissue samples from a plurality of the seeds in the population using an automated seed sampler system while preserving the germination viability of the sampled seeds, and analyzing the tissue samples for the presence or absence of one or more characteristics indicative of at least one genetic or chemical trait.

26 Claims, 2 Drawing Sheets

U.S. PATENT DOCUMENTS

| | | | |
|---|---|---|---|
| 3,350,372 A | 10/1967 | Anspon et al. |
| 3,530,372 A | 9/1970 | Laukien |
| 3,642,128 A | 2/1972 | Westwood et al. |
| 3,852,914 A | 12/1974 | Levengood |
| 3,861,788 A | 1/1975 | Webster |
| 4,037,970 A | 7/1977 | Webster et al. |
| 4,040,747 A | 8/1977 | Webster |
| 4,260,262 A | 4/1981 | Webster |
| 4,278,183 A | 7/1981 | Billington |
| 4,375,854 A | 3/1983 | Hedel |
| 4,480,765 A | 11/1984 | Tonus |
| 4,654,592 A | 3/1987 | Zens |
| 4,696,308 A | 9/1987 | Meller et al. |
| 4,734,584 A | 3/1988 | Rosenthal |
| 4,752,689 A | 6/1988 | Satake et al. |
| 4,818,380 A | 4/1989 | Azegami et al. |
| 4,827,776 A | 5/1989 | Gale et al. |
| 4,884,696 A | 12/1989 | Peleg |
| 4,931,061 A | 6/1990 | Young |
| 4,946,046 A | 8/1990 | Affleck et al. |
| 5,051,699 A | 9/1991 | Hanawa et al. |
| 5,132,538 A | 7/1992 | Norris |
| 5,221,518 A | 6/1993 | Mills |
| 5,245,188 A | 9/1993 | Satake et al. |
| 5,253,302 A | 10/1993 | Massen |
| 5,412,220 A | 5/1995 | Moore |
| 5,416,011 A | 5/1995 | Hinchee et al. |
| 5,437,697 A | 8/1995 | Sebastian et al. |
| 5,475,221 A | 12/1995 | Wang |
| 5,533,145 A | 7/1996 | Shofner et al. |
| 5,569,834 A | 10/1996 | Hinchee et al. |
| 5,590,791 A | 1/1997 | Gschweitl |
| 5,668,374 A | 9/1997 | DiFoggio et al. |
| 5,669,511 A | 9/1997 | Satake et al. |
| 5,677,474 A | 10/1997 | Rogers |
| 5,733,592 A | 3/1998 | Wettstein et al. |
| 5,746,023 A | 5/1998 | Hanafey et al. |
| 5,751,421 A | 5/1998 | Wright et al. |
| 5,764,819 A | 6/1998 | Orr et al. |
| 5,824,877 A | 10/1998 | Hinchee et al. |
| 5,833,947 A | 11/1998 | Rocklage et al. |
| 5,836,438 A | 11/1998 | Jung |
| 5,837,458 A | 11/1998 | Minshull et al. |
| 5,864,984 A | 2/1999 | McNertney |
| 5,914,451 A | 6/1999 | Martinell et al. |
| 5,918,977 A | 7/1999 | Borggaard et al. |
| 5,991,025 A | 11/1999 | Wright et al. |
| 6,100,526 A | 8/2000 | Mayes |
| 6,150,158 A | 11/2000 | Bhide et al. |
| 6,237,286 B1 | 5/2001 | Williams |
| 6,266,864 B1 | 7/2001 | Barber |
| 6,384,301 B1 | 5/2002 | Martinell et al. |
| 6,397,678 B1 | 6/2002 | Popper |
| 6,537,826 B1 | 3/2003 | Horigane et al. |
| 6,646,264 B1 | 11/2003 | Modiano et al. |
| 6,705,827 B2 | 3/2004 | Keller et al. |
| 6,706,989 B2 | 3/2004 | Hunter et al. |
| 6,782,991 B2 | 8/2004 | Johansson |
| 6,809,819 B1 | 10/2004 | Vinjamoori et al. |
| 6,879,389 B2 | 4/2005 | Meyer et al. |
| 6,947,144 B2 | 9/2005 | Kim et al. |
| 6,959,617 B2 | 11/2005 | Deppermann |
| 7,002,058 B2 | 2/2006 | Martinell et al. |
| 7,044,306 B2 | 5/2006 | Deppermann |
| 7,123,750 B2 | 10/2006 | Lu et al. |
| 7,367,155 B2 | 5/2008 | Kotyk et al. |
| 7,403,855 B2 | 7/2008 | Fuessley et al. |
| 7,502,113 B2 | 3/2009 | Deppermann et al. |
| 7,591,101 B2 | 9/2009 | Deppermann |
| 7,611,842 B2 | 11/2009 | Deppermann et al. |
| 7,703,238 B2 * | 4/2010 | Deppermann et al. ..... 47/58.1 R |
| 7,767,883 B2 | 8/2010 | Deppermann et al. |
| 7,830,516 B2 | 11/2010 | Deppermann et al. |
| 7,832,143 B2 | 11/2010 | Deppermann et al. |
| 7,849,632 B2 | 12/2010 | Deppermann et al. |
| 7,877,926 B2 | 2/2011 | Deppermann et al. |
| 7,941,969 B2 | 5/2011 | Deppermann et al. |
| 7,998,669 B2 | 8/2011 | Deppermann et al. |
| 8,028,469 B2 | 10/2011 | Deppermann et al. |
| 8,071,845 B2 | 12/2011 | Deppermann |
| 2001/0013486 A1 | 8/2001 | Yamakawa |
| 2001/0014750 A1 | 8/2001 | Ulrich et al. |
| 2001/0024796 A1 | 9/2001 | Selifonov et al. |
| 2002/0144458 A1 | 10/2002 | Hunter et al. |
| 2003/0142852 A1 | 7/2003 | Lu et al. |
| 2003/0148258 A1 | 8/2003 | Kim et al. |
| 2003/0188998 A1 | 10/2003 | Deppermann |
| 2004/0091888 A1 | 5/2004 | Nishio et al. |
| 2004/0141641 A1 | 7/2004 | McDonald et al. |
| 2004/0160607 A1 | 8/2004 | Lin et al. |
| 2004/0221335 A1 | 11/2004 | Shewmaker et al. |
| 2005/0005321 A1 | 1/2005 | Martinell et al. |
| 2005/0082207 A1 | 4/2005 | Deppermann |
| 2005/0154221 A1 | 7/2005 | Lysenko et al. |
| 2006/0004624 A1 | 1/2006 | Melara et al. |
| 2006/0042527 A1 | 3/2006 | Deppermann |
| 2006/0042528 A1 | 3/2006 | Deppermann |
| 2006/0046244 A1 | 3/2006 | Deppermann |
| 2006/0046264 A1 | 3/2006 | Deppermann et al. |
| 2006/0048247 A1 | 3/2006 | Deppermann |
| 2006/0112628 A1 | 6/2006 | Kotyk et al. |
| 2007/0048872 A1 | 3/2007 | Deppermann et al. |
| 2007/0204366 A1 | 8/2007 | Deppermann et al. |
| 2007/0207485 A1 | 9/2007 | Deppermann et al. |
| 2007/0240241 A1 | 10/2007 | Ubach et al. |
| 2007/0240242 A1 | 10/2007 | Modiano et al. |
| 2008/0000815 A1 | 1/2008 | Deppermann |
| 2008/0113367 A1 | 5/2008 | Becker et al. |
| 2008/0131254 A1 | 6/2008 | Cope et al. |
| 2008/0131924 A1 | 6/2008 | Cope et al. |
| 2008/0203201 A1 | 8/2008 | Deppermann et al. |
| 2008/0243392 A1 | 10/2008 | Fuessley et al. |
| 2008/0310674 A1 | 12/2008 | Modiano et al. |
| 2008/0317279 A1 | 12/2008 | Deppermann et al. |
| 2009/0025288 A1 | 1/2009 | Deppermann et al. |
| 2009/0032441 A1 | 2/2009 | Corak et al. |
| 2009/0215060 A1 | 8/2009 | Deppermann et al. |
| 2010/0044356 A1 | 2/2010 | Cope |
| 2010/0086963 A1 | 4/2010 | Deppermann et al. |
| 2010/0196950 A1 | 8/2010 | Deppermann et al. |
| 2010/0263087 A1 | 10/2010 | Deppermann et al. |
| 2011/0217700 A1 | 9/2011 | Deppermann et al. |
| 2011/0296930 A1 | 12/2011 | Deppermann et al. |
| 2012/0021411 A1 | 1/2012 | Deppermann et al. |
| 2012/0079629 A1 | 3/2012 | Deppermann et al. |
| 2012/0117865 A1 | 5/2012 | Deppermann et al. |

FOREIGN PATENT DOCUMENTS

| | | |
|---|---|---|
| CL | 673-03 | 2/2004 |
| CL | 2190-05 | 5/2007 |
| DE | 19845883 | 5/1999 |
| DE | 10048643 | 5/2001 |
| DE | 102004063769 | 7/2006 |
| EP | 0539537 B2 | 5/1993 |
| EP | 0636310 A1 | 2/1995 |
| EP | 0730164 | 9/1996 |
| EP | 0750188 | 12/1996 |
| EP | 0511184 B1 | 6/1998 |
| EP | 2 279 658 | 2/2011 |
| FR | 2549963 | 2/1985 |
| GB | 1151988 A2 | 5/1969 |
| GB | 1355612 | 6/1974 |
| GB | 1408458 | 10/1975 |
| GB | 1471076 | 4/1977 |
| JP | 406284806 | 10/1994 |
| JP | 10-319106 | 12/1998 |
| RU | 2229210 | 5/2004 |
| SU | 536785 | 11/1976 |
| SU | 1658858 | 6/1991 |
| SU | 1805835 A3 | 3/1993 |
| WO | WO-96/24830 | 8/1996 |
| WO | WO-97/00887 | 1/1997 |
| WO | WO-98/14046 A1 | 4/1998 |
| WO | WO-98/44140 | 10/1998 |
| WO | WO-99/40419 | 8/1999 |
| WO | WO-99/41383 | 8/1999 |
| WO | WO-99/58959 | 11/1999 |

| WO | WO-00/52990 | 9/2000 |
| WO | WO-00/71993 A1 | 11/2000 |
| WO | WO-01/22043 | 3/2001 |
| WO | WO-01/44828 | 6/2001 |
| WO | WO-01/89288 A1 | 11/2001 |
| WO | WO-02/16090 | 2/2002 |
| WO | WO-02/48687 | 6/2002 |
| WO | WO-02/059586 | 8/2002 |
| WO | WO-02/071040 | 9/2002 |
| WO | WO-03/084847 | 10/2003 |
| WO | WO-03/100381 | 12/2003 |
| WO | WO-2004/063333 | 7/2004 |
| WO | WO 2005/031367 | 5/2005 |
| WO | WO-2006/026466 | 3/2006 |
| WO | WO-2006/026467 | 3/2006 |
| WO | WO 2012/012411 | 1/2012 |

OTHER PUBLICATIONS

McGinty et al. "A System for Automatic Weight Determination of Individual Grain Kernels: Principles and Evaluation," *Cereal Chem.* 19(5):196-199 (1974).

Morrison, *Sampling in Seed Health Testing*, The American Phytopathology, 1999, 89: 1084-1087.

Orman and Schumann, "Comparison of Near-Infrared Spectroscopy Calibration Methods for the Prediction of Protein, Oil, and Starch in Maize Grain," J. Agric. Food Chem. vol. 39, 1991, pp. 883-886.

P.A. Hailey—Pfizer Central Research, "The Role of NIR Spectroscopy in the Measurement of Pharmaceutical Manufacture", <http://www.brimrose.com.hailey.html>.

Paige et al. "Apparatus for Automatic Measurement of Kernel Weight, Length, and Thickness," *Crop Sci. 31*:1314-1318 (1991).

Pioneer Hi-Bred International, Inc., Downloadable Photos—Laser-Assisted Seed Selection, <http://www.pioneer.com/web/site/portal/menuiteam.b9e99dcb8e2cfd8ecfe6d10093a0/>, printed as of Nov. 25, 2008, 4 pages.

PR Newswire, Monsanto Collaborates with Foss to Develop Analytical Tools for Soybeans, Installs Improved Low-Linolenic Calibration System for 2007 Fall Harvest, Sep. 20, 2007, 3 pages.

Rapid Identification of Organic Contaminants in Retreated Waste Water Using AOTF near-IR Spectrometry, *ISA1995 Meeting Proceedings*, pp. 87-95, 1995.

Robutti, "Maize Kernel Hardness Estimation in Breeding by Near-Infrared Transmission Analysis," Analytical Techniques and Instrumentation vol. 72, No. 6, 1995, pp. 632-636.

Rubel et al. "Simultaneous Determination of Oil and Water Contents in Different Oilseeds by Pulsed Nuclear Magnetic Resonance," *JAOCS 71*(10):1057-1062 (1994).

Saito et al. "Application of Magnetic Resonance Imaging to Non-Destructive Void Detection in Watermelon," *Cryogenics* 36(12):1027-1031 (1996).

Sander et al., "System for Automatic Weight Determination of Individual Grain Kernels," *Transactions of the ASAE*, pp. 1146-1147 (1973).

Schuster Ivan et all, "Correlation between high molecular weight gluten subunits composition and bread-making quality in Brazilian wheat," Brazilian Journal of Genetics, vol. 20, No. 4, Dec. 1997, pp. 667-671.

Sedcole, J.R. "Number of plants necessary to recover a trait," Crop Sci. 17:667-68 (1977).

Seed Meister Luminar 3076, Brimrose Corporation of America, Baltimore, MD, <http://www.brimrose.com/seed_meister.html>.

Serial Extraction of Endosperm Drillings (SEED)—A Method for Detecting Transgenes and Proteins in Single Viable Maize Kernels, Varaporn Sangton, et al., Plant Molecular Biology Reporter 19: 151-158, Jun. 2001, International Society for Plant Molecular Biology.

Siebenmorgen et al. "A Data Acquisition/Control System for Individual Kernel and Thin-Layer Grain Drying Research" *Am. Soc. of Agri. Engrs., Univ. of Ark., 1991 Int'l Summer Meeting, Paper 91-3042*, pp. 1-16 (1991).

Borevitz et al., (2003) Large-Scale Identification of Single-Feature Polymorphisms in Complex Genomes, Gen. Res. 13:513-523.

Archibald et al., "Development of Short-Wavelength Near-Infrared Spectral Imaging for Grain Color Classification," SPIE vol. 3543, 1998, pp. 189-198.

Bauman et al., Inheritance of Variations in Oil Content of Individual Corn (*Zea mays* L.) Kernels, *Crop Science*, 5:137-138 (1965).

Brumback, Jr., et al., "Automating fatty acid analyses from seeds: from field samples to data bases," Lab. Inf. Manage., 21 (1993) pp. 215-222.

Cabrera et al., Open Storage of Soybean Seed in Mississippi, Mississippi Agricultural and Forestry Experiment Station, Sep. 2002. <http://msucares.com/pubs/techbulletins/tb204.htm>.

Callaway A. S. et al., "High-Throughput Transgene Copy Number Estimation by Competitive PCR", Plant Molecular Biology Reporter, vol. 20, Sep. 2002, pp. 265-277.

Chunwongse J. et al., "Pre-germination genotyping screening using PCR amplification of half-seeds" Theoretical and Applied Genetics, Springer, Berlin, DE, vol. 86, No. 6, Jan. 1993, pp. 694-698.

Dahmer et al., "A Rapid Screening Technique for Determining the Lipid Composition of Soybean Seeds", Journal of the American Oil Chemists' Society, Springer, Berlin, DE, vol. 66, Jan. 1989, pp. 543-549.

Daun et al., "Comparison of Three Whole Seed Near-Infrared Analyzers for Measuring Quality Components of Canola Seed", vol. 71, No. 10, 1994, pp. 1063-1068.

Dellaporta et al., A Plant DNA Minipreparation: Version II, Plant Molecular Biology Reporter, vol. 1, No. 4, pp. 19-21 (1983).

Delwiche, "Single Wheat Kernel Analysis by Near-Infrared Transmittance: Protein Content," Analytical Techniques and Instrumentation, vol. 72, No. 1, 1995, pp. 11-16.

Demidov Dimitri et al., "Additive effects of the feed-back insensitive bacterial aspartate kinase and the Brazil nut 2S albumin on the methionine content of transgenic narbon bean (*Vicia narbonensis* L.).", Molecular Breeding, vol. 11, No. 3, Apr. 2003, pp. 187-201.

Dowell et al., "Automated Single Wheat Kernel Quality Measurement Using Near-Infrared Reflectance," ASAE Annual International Meeting, 1997, paper No. 973022.

Dowell, "An Intelligent Automated System for Determining Peanut Quality," *IEEE International Workshop on Intelligent Robots and Sytems, IROS*, pp. 237-241 (1990).

Dowell, "Automated Color Classification of Single Wheat Kernels Using Visible and Near-Infrared Reflectance," Cereal Chemistry, vol. 75(1), 1998, pp. 142-144.

Dr. Jolanta Soos, "Industrial Process Monitoring Requires Rugged AOTF Tools", *Laser Focus World*, Aug. 1994.

Gambhir et al. "Simultaneous Determination of Moisture and Oil Content in Oilseeds by Pulsed Nuclear Magnetic Resonance," *JAOCS*, 62(1):103-108 (1985).

Gasbarra et al. "Constructing the Parental Linkage Phase and the Genetic Map Over Distances <1 cM Using Pooled Haploid DNA", Genetics 172:1325-1335 (2006).

Gillaspie, Jr., Sensitive Method for Testing Peanut Seed Lots for Peanut Stripe and Peanut Mottle Viruses by Immunocapture-Reverse Transcription-Polymerase Chain Reaction, Plant Disease, May 2000, pp. 559-561.

Guidetti Geri, Viability Myths, <http://waltonfeed.com/self/upack/ag506a1.html>, (2007), 4 pages.

Halloin et al. "Proton Magnetic Resonance Imaging of Lipid in Pecan Embryos," *JAOCS*, 70(12):1259-1262 (1993).

Heil et al. "Magnetic Resonance Imaging and Modeling of Water Up-take into Dry Beans," *Lebensm-Wiss u-Technol*, 25:280-285 (1992).

Higley P M et al., "Evaluation of Seed Biopsy Methods for Nondestructive Seed Health Testing", Phytopathology, St. Paul, MN, US, vol. 79, No. 10, Jan. 1989, p. 1140.

J.P. Hazebroek, "Analysis of genetically modified oils" Progress in Lipid Research 39 (2000) pp. 477-506.

Jones D A L M Barber et al., "An analysis of seed development in *Pisum sativum* L. XVI. Assessing variation for fatty acid content by use of a non-destructive technique for single-seed analysis", Plant Breeding, vol. 114, No. 1, 1995, pp. 81-83.

Karcz Jagna et al., "Structural and embryological studies of diploid and tetraploid *Arabidopsis thaliana* (L.) Heynah", Acta Biologica Cracoviensia Series Botanica, vol. 42, No. 2, 2000, pp. 113-124.

Kotyk et al., High-Throughput Determination of Oil Content in Corn Kernels Using Nuclear Magnetic Resonance Imaging, JAOCS, vol. 82, No. 12, 2005, pp. 855-862.

Kramer et al., *Transgenic Avidin Maize is Resistant to Storage Insect Pests*, Nature Biotechnology, vol. 18, Jun. 2000, pp. 670-674.

Krisnangkura K. et al., "Continuous transmethylation of palm oil in an organic solvent", Jaoch, vol. 69, 1992.

Krysan, Breakthrough Technologies, Ice-Cap. A High-Throughput Method for Capturing Plant Tissue Samples for Genotype Analysis, Plant Physiology, Jul. 2004 vol. 135, pp. 1162-1169.

Lakshminarayana et al. "Spatial distribution of oil in groundnut and sunflower seeds by nuclear magnetic resonance imaging," *J. Biosci* 17(1):87-93 (1992).

MacNamara et al., "Multiplex sample NMR: an approach to high-throughput NMR using a parallel coil probe," *Analytica Chimica Acta*, 397:9-16 (1999).

Massie and Norris, "Spectral Reflectance and Transmittance Properties of Grain in the Visible and Near Infrared", Transactions of the ASAE, Winter Meeting of the American Society of Agricultural Engineers, 1965, pp. 598-600.

McCarthy Paul L. et al., "Rapid identification of transformed wheat using a half-seed PCR assay," Biotechniques, vol. 32, No. 3, Mar. 2002, pp. 560-564.

Smith et al., Genetic Purity and Testing Technologies for Seed Quality: A Company Perspective, Seed Science Research, 1998, vol. 8, pp. 285-293.

Song et al., "Non-invasive Measurement of Moisture Distribution in Individual Wheat Kernels by Magnetic Resonance Imaging," *SPIE*, 2345:414-422 (1994).

Soybean Cyst Nematode, Plant Pathology, Iowa State University, University Extension, Ames, Iowa, Pm-879, Revised Oct. 1995, 6 pages.

Van Der Mey J A M et al., "Mass Screening for Alkaloid Content in Lupinus-Albus", Applied Plant Science, vol. 1, No. 2, 1987, pp. 80-82.

Von Post et al., A High-Throughput DNA Extraction Method for Barley Seed, Euphytica 130: 255-260, 2003.

Yoshida et al., "An automatic sequential single-seed weighing system: variation in soybean seed weight," *J. Fac. Agr. Hokkaido Univ.* 61(2):225-232 (1982).

Zeile, W.L. et al., "A Rapid Non-Destructive Technique for Fatty Acid Determination in Individual Peanut Seed" Peanut Science (1993) 20:9-11 (3 pages).

\* cited by examiner

METHODS OF SEED BREEDING USING HIGH THROUGHPUT NONDESTRUCTIVE SEED SAMPLING

CROSS-REFERENCE TO RELATED APPLICATIONS

This application is a continuation of U.S. patent application Ser. No. 12/767,640 filed Apr. 26, 2010, which is a continuation of U.S. patent application Ser. No. 11/680,611 filed Feb. 28, 2007 (now U.S. Pat. No. 7,703,238 issued Apr. 27, 2010), which claims priority to U.S. Provisional Application Ser. No. 60/778,828 filed Mar. 2, 2006, and which is a continuation-in-part of U.S. patent application Ser. No. 11/213,435 filed Aug. 26, 2005 (now U.S. Pat. No. 7,611,842 issued Nov. 3, 2009). U.S. patent application Ser. No. 11/213,435 claims priority to U.S. Provisional Application Ser. No. 60/604,604 filed Aug. 26, 2004, and U.S. Provisional Application Ser. No. 60/691,100 filed Jun. 15, 2005. The entire disclosures of all of the above applications are incorporated herein by reference.

FIELD

The present invention relates to the field of plant breeding. More specifically, this invention provides methods for augmenting and economizing germplasm improvement activities using high throughput and nondestructive seed sampling techniques.

BACKGROUND

The statements in this section merely provide background information related to the present disclosure and may not constitute prior art.

In plant development and improvement, genetic improvements are made in the plant, either through selective breeding or genetic manipulation, and when a desirable improvement is achieved, a commercial quantity is developed by planting and harvesting seeds over several generations. To speed up the process of plant improvement, statistical samples are taken and tested to advance seeds from the population that have inherited or exhibit the desired trait. However this statistical sampling necessarily allows some seeds without the desirable trait to remain in the population, and also can inadvertently exclude some seeds with the desirable trait from the desired population. Not all seeds inherit or exhibit the desired traits, and thus these seeds still need to be culled from the population.

Apparatus and methods for the high-throughput, non-destructive sampling of seeds have been described which would overcome the obstacles of statistical samples by allowing for individual seed analysis. For example, U.S. patent application Ser. No. 11/213,430 (filed Aug. 26, 2005); U.S. patent application Ser. No. 11/213,431 (filed Aug. 26, 2005); U.S. patent application Ser. No. 11/213,432 (filed Aug. 26, 2005); U.S. patent application Ser. No. 11/213,434 (filed Aug. 26, 2005); and U.S. patent application Ser. No. 11/213,435 (filed Aug. 26, 2005), which are incorporated herein by reference in their entirety, disclose apparatus and systems for the automated sampling of seeds as well as methods of sampling, testing and bulking seeds.

The present invention addresses needs in the art for improved breeding methods using high-throughput, non-destructive seed sampling systems.

SUMMARY

The present disclosure relates to systems and methods for facilitating germplasm improvement activities through the use of high throughput, nondestructive sampling of seeds. With automated, non-destructive sampling, it is possible to test individual seeds in a population, and select only the seeds that possess one or more desired characteristics. This allows for new and more efficient methods for germplasm improvement and management, which lead to improved breeding populations.

In one embodiment, the present disclosure provides for a high-throughput, non-destructive method for analyzing individual seeds in a population of seeds. The method comprises removing a sample from a plurality of seeds in the population while preserving the germination viability of the seed and analyzing the sample for the presence or absence of one or more characteristics indicative of at least one genetic or chemical trait.

In a further embodiment, the present disclosure provides for a high-throughput method for analyzing a population of haploid seed. The method comprises removing a sample from a plurality of seeds in a population of haploid seed while preserving the germination viability of the seed and analyzing the samples for the presence or absence of one or more characteristics indicative of at least one genetic or chemical trait.

In a still further embodiment, the present disclosure provides for a high-throughput method for bulking a population of doubled haploid seed. The method comprises providing a population of seeds comprising haploid seeds and selecting one or more individual seeds exhibiting at least one preferred characteristic from the population of seeds. Doubled haploid seeds are then produced from the selected seeds and a sample is removed from each doubled haploid seed while preserving the germination viability of the seeds. The samples are analyzed for the presence or absence of one or more characteristics indicative of at least one genetic or chemical trait. Based on the results of the analysis, one or more individual doubled haploid seeds are selected and plants or plant tissue is cultivated from the selected doubled haploid seed.

In the various embodiments of the present invention, the samples may be analyzed for one or more characteristics indicative of at least one chemical trait. Examples of such characteristics may include proteins, oils, carbohydrates, fatty acids, amino acids, biopolymers, pharmaceuticals, starch, fermentable starch, secondary compounds, and metabolites.

In other various embodiments of the present invention, the samples may be analyzed for one or more characteristics indicative of at least one genetic trait. Examples of such characteristics may include a genetic marker, a single nucleotide polymorphism, a simple sequence repeat, a restriction fragment length polymorphism, a haplotype, a tag SNP, an alleles of a genetic marker, a gene, a DNA-derived sequence, an RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation pattern.

Further areas of applicability of the present teachings will become apparent from the description provided herein. It should be understood that the description and specific examples are intended for purposes of illustration only and are not intended to limit the scope of the present teachings.

BRIEF DESCRIPTION OF THE DRAWINGS

The drawings described herein are for illustration purposes only and are not intended to limit the scope of the present disclosure in any way.

DETAILED DESCRIPTION

Figure 1:
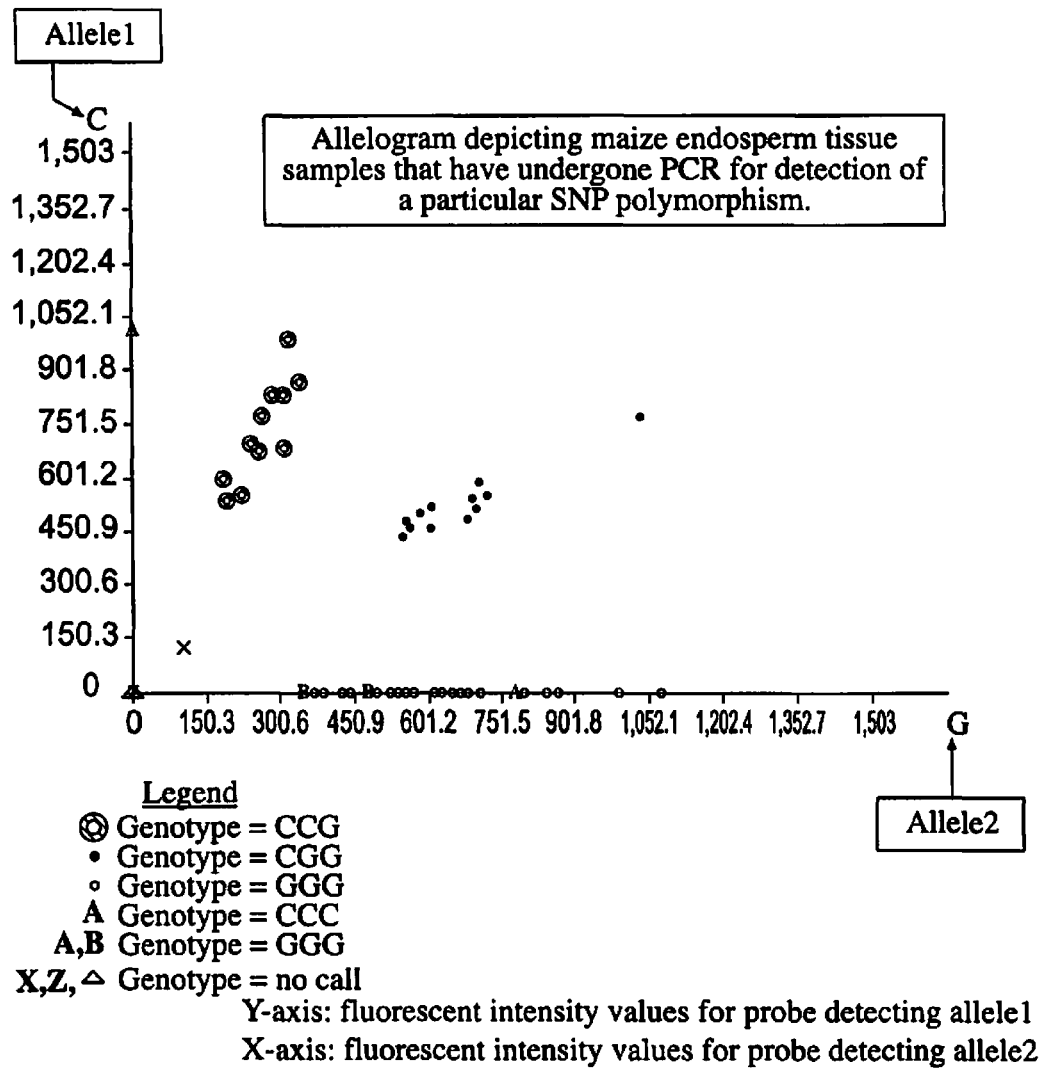
FIG. 1 is an allelogram depicting maize endosperm tissue samples that have undergone PCR for detection of a particular SNP as described in Example 3.

The following description is merely exemplary in nature and is not intended to limit the present disclosure, application, or uses.

The present invention provides for novel methods to facilitate germplasm improvement activities through the use of high throughput, nondestructive sampling of seeds. The methods are useful in analyzing seeds in order to identify and select seeds comprising one or more desired traits, markers, and genotypes. In one aspect of the invention, the analytical methods allow individual seeds that are present in a batch or a bulk population of seeds to be analyzed such that the chemical and/or genetic characteristics of the individual seeds can be determined.

Samples prepared by the present invention can be used for determining a wide variety of physical, morphological, chemical and/or genetic traits. Generally, such traits are determined by analyzing the samples for one or more characteristics indicative of at least one genetic or chemical trait. Non-limiting examples of characteristics indicative of chemical traits include proteins, oils, carbohydrates, fatty acids, amino acids, biopolymers, pharmaceuticals, starch, fermentable starch, secondary compounds, and metabolites. Accordingly, non-limiting examples of chemical traits include amino acid content, protein content, starch content, fermentation yield, fermentation efficiency, energy yield, oil content, determination of protein profiles determination of fatty acid profiles, determination of metabolite profiles, etc.

Non-limiting examples of characteristics indicative of genetic traits may include, for example, genetic markers, single nucleotide polymorphisms, simple sequence repeats, restriction fragment length polymorphisms, haplotypes, tag SNPs, alleles of genetic markers, genes, DNA-derived sequences, RNA-derived sequences, promoters, 5' untranslated regions of genes, 3' untranslated regions of genes, microRNA, siRNA, quantitative trait loci (QTL), satellite markers, transgenes, mRNA, ds mRNA, transcriptional profiles, and methylation patterns.

In one embodiment, the sampling of endosperm tissue enables the determination of allele frequencies, whereby it is possible to infer parental linkage phase for a particular marker. Further, comparison of allele frequency data between two or more germplasm pools provides insight into the targets of selection, whereby alleles increasing in frequency in conjunction with a shift in distribution of one or more traits are presumed to be linked to said trait or traits of interest. Also, evaluation of relative allele frequency data between lines can contribute to the construction of genetic linkage maps.

In another embodiment, the methods of the present invention use high throughput, nondestructive seed sampling with doubled haploid technologies to contribute to germplasm improvement activities including economization of doubled haploid programs by selecting only preferred seed for doubling, high throughput analysis of haploid and doubled haploid material for both genotypic and chemical characteristics, trait integration and evaluation, and marker-assisted breeding.

The methods and devices of the present invention can be used in a breeding program to select plants or seeds having a desired genetic or chemical trait, wherein a desired genetic trait comprises a genotype, a haplotype, an allele, a sequence, a transcript profile, and a methylation pattern. The methods of the present invention can be used in combination with any breeding methodology and can be used to select a single generation or to select multiple generations. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches for breeding the plants of the present invention are set forth below. It is further understood that any commercial and non-commercial cultivars can be utilized in a breeding program. Factors including, for example, without limitation, emergence vigor, vegetative vigor, stress tolerance, disease resistance, branching, flowering, seed set, seed size, seed density, standability, and threshability will generally dictate the choice.

In a particular embodiment, the methods of the present invention are used to determine the genetic characteristics of seeds in a marker-assisted breeding program. Such methods allow for improved marker-assisted breeding programs wherein nondestructive direct seed sampling can be conducted while maintaining the identity of individual seeds from the seed sampler to the field. As a result, the marker-assisted breeding program results in a "high-throughput" and more efficient platform wherein a population of seeds having a desired trait, marker or genotype can be more effectively bulked in a shorter period of time, with less field and labor resources required. Such advantages will be more fully described below.

In one embodiment, the present invention provides a method for analyzing individual seeds within a population of seeds having genetic differences. The method comprises removing a sample comprising cells with nucleic acids from seeds in the population without affecting the germination viability of the seeds; analyzing the nucleic acids extracted from the sample for the presence or absence of at least one genetic marker; selecting seeds from the population based upon the results of the nucleic acid analysis; and cultivating plants from the selected seed.

As described above, the sampling systems and methods of this invention protect germination viability of the seeds so as to be non-destructive. Germination viability means that a predominant number of sampled seeds, (i.e., greater than 50% of all sampled seeds) remain viable after sampling. In a particular embodiment, at least about 75% of sampled seeds, and in some embodiments at least about 85% of sampled seeds remain viable. It should be noted that lower rates of germination viability may be tolerable under certain circumstances or for certain applications, for example, as genotyping costs decrease with time because a greater number of seeds could be sampled for the same genotype cost. It should also be noted that sampling does not need to have any effect on viability at all.

In another embodiment, germination viability is maintained for at least about six months after sampling to ensure that the sampled seed will be viable until it reaches the field for planting. In a particular embodiment, the methods of the present invention further comprise treating the sampled seeds to maintain germination viability. Such treatment may generally include any means known in the art for protecting a seed from environmental conditions while in storage or transport. For example, in one embodiment, the sampled seeds may be treated with a polymer and/or a fungicide to protect the sampled seed while in storage or in transport to the field before planting.

In one embodiment, the samples of the present invention are used in a high-throughput, non-destructive method for analyzing individual seeds in a population of seeds. The method comprises removing a sample from the seed while preserving the germination viability of the seed; and analyzing the sample for the presence or absence of one or more characteristics indicative of a genetic or chemical trait. The method may further comprise selecting seeds from the population based on the results of the analysis; and cultivating plants or plant tissue from the selected seed.

DNA may be extracted from the sample using any DNA extraction methods known to those of skill in the art which will provide sufficient DNA yield, DNA quality, PCR response, and sequencing methods response. A non-limiting example of suitable DNA-extraction methods is SDS-based extraction with centrifugation. In addition, the extracted DNA may be amplified after extraction using any amplification method known to those skilled in the art. For example, one suitable amplification method is the GenomiPhi® DNA amplification prep from Amersham Biosciences.

Further, RNA may be extracted from the sample using any RNA extraction methods known to those of skill in the art which will provide sufficient RNA yield, RNA quality, PCR response, and sequencing methods response. A non-limiting example of suitable RNA-extraction methods is SDS-based extraction with centrifugation with consideration for RNase-free reagents and supplies. In addition, the extracted RNA may be amplified after extraction using any amplification method known to those skilled in the art. For example, one suitable amplification method is the Full Spectrum™ RNA Amplification from System Biosciences.

The extracted nucleic acids are analyzed for the presence or absence of a suitable genetic polymorphism. A wide variety of genetic markers for the analysis of genetic polymorphisms are available and known to those of skill in the art. As used herein, genetic markers include, but are not limited to, simple sequence repeats (SSRs), single nucleotide polymorphisms (SNPs), insertions or deletions (Indels), single feature polymorphisms (SFPs, for example, as described in Borevitz et al. 2003 Gen. Res. 13:513-523) or transcriptional profiles, and nucleic acid sequences. A nucleic acid analysis for the presence or absence of the genetic marker can be used for the selection of seeds in a breeding population. The analysis may be used to select for genes, QTL, alleles, or genomic regions (haplotypes) that comprise or are linked to a genetic marker. Herein, analysis methods are known in the art and include, but are not limited to, PCR-based detection methods (for example, TaqMan assays), microarray methods, and nucleic acid sequencing methods. The genes, alleles, QTL, or haplotypes to be selected for can be identified using newer techniques of molecular biology with modifications of classical breeding strategies.

Any seed can be utilized in a method or device of the present invention. In a particular embodiment, the seed is selected from the group consisting of alfalfa seed, apple seed, banana seed, barley seed, bean seed, broccoli seed, castor-bean seed, citrus seed, clover seed, coconut seed, coffee seed, maize seed, cotton seed, cucumber seed, Douglas fir seed, Eucalyptus seed, Loblolly pine seed, linseed seed, melon seed, oat seed, olive seed, palm seed, pea seed, peanut seed, pepper seed, poplar seed, Radiata pine seed, rapeseed seed, rice seed, rye seed, sorghum seed, Southern pine seed, soybean seed, strawberry seed, sugarbeet seed, sugarcane seed, sunflower seed, sweetgum seed, tea seed, tobacco seed, tomato seed, turf seed, wheat seed, and *Arabidopsis thaliana* seed. In a more particular embodiment, the seed is selected from the group consisting of cotton seed, cucumber seed, maize seed, melon seed, soybean seed, rapeseed seed, rice seed and wheat seed. In an even more particular embodiment, the seed is a maize seed or a soybean seed.

In another embodiment, crops analyzed by the methods described herein include forage crops, oilseed crops, grain crops, fruit crops, ornamental plants, vegetable crops, fiber crops, spice crops, nut crops, turf crops, sugar crops, beverage crops, tuber crops, root crops, and forest crops.

In one embodiment, the seed is selected based on the presence or absence of one or more characteristics that are genetically linked with a QTL. Examples of QTLs which are often of interest include but are not limited to herbicide tolerance, disease resistance, insect or pest resistance, altered fatty acid, protein or carbohydrate metabolism, increased grain yield, increased oil, increased nutritional content, increased growth rates, enhanced stress tolerance, preferred maturity, enhanced organoleptic properties, altered morphological characteristics, other agronomic traits, traits for industrial uses, or traits for improved consumer appeal, or a combination of traits as a multiple trait index. Alternatively, the seed can be selected based on the presence or absence of one or more characteristics that are genetically linked with a haplotype associated with a QTL. Examples of such QTL may again include without limitation herbicide tolerance, disease resistance, insect or pest resistance, altered fatty acid, protein or carbohydrate metabolism, increased grain yield, increased oil, increased nutritional content, increased growth rates, enhanced stress tolerance, preferred maturity, enhanced organoleptic properties, altered morphological characteristics, other agronomic traits, traits for industrial uses, or traits for improved consumer appeal, or a combination of traits as a multiple trait index.

Selection of a breeding population could be initiated as early as the $F_2$ breeding level, if homozygous inbred parents are used in the initial breeding cross. An $F_1$ generation could also be sampled and advanced if one or more of the parents of the cross are heterozygous for the alleles or markers of interest. The breeder may analyze an $F_2$ population to retrieve the marker genotype of every individual in the population. Initial population sizes, limited only by the number of available seeds for analysis, can be adjusted to meet the desired probability of successfully identifying the desired number of individuals. See Sedcole, J. R. "Number of plants necessary to recover a trait." *Crop Sci.* 17:667-68 (1977). Accordingly, the probability of finding the desired genotype, the initial population size, and the targeted resulting population size can be modified for various breeding methodologies and inbreeding level of the sampled population.

The selected seeds may be bulked or kept separate depending on the breeding methodology and target. For example, when a breeder is analyzing an $F_2$ population for disease resistance, all individuals with the desired genotype may be bulked and planted in the breeding nursery. Conversely, if multiple QTL with varying effects for a trait such as grain yield are being selected from a given population, the breeder may keep individual identity preserved, going to the field to differentiate individuals with various combinations of the target QTL.

Several methods of preserving single seed identity can be used while transferring seed from the sampling location to the field. Methods include, but are not limited to, transferring selected individuals to seed tape, a cassette tray, or indexing tray, transplanting with peat pots, and hand-planting from individual seed packets.

Multiple cycles of selection can be utilized depending on breeding targets and genetic complexity.

Advantages of using the methods of this invention include, without limitation, reduction of labor and field resources required per population or breeding line, increased capacity to evaluate a larger number of breeding populations per field unit, and increased capacity to analyze breeding populations for desired traits prior to planting. Field resources per population are reduced by limiting the field space required to advance the desired genotypes. For example, a population of 1,000 individuals may be planted at 25 seeds per row consuming a total of 40 rows in the field. Using conventional tissue sampling, all 1,000 plants would be tagged and manually sampled by scoring leaf tissue. Molecular marker results would be needed prior to pollination and only those plants containing the desired genetic composition would be pollinated. Thus, if it was determined that 50 seeds contained the desired genetic composition, conventional breeding methodology would have required the planting of 1000 plants to retain the desired 50 seeds. By contrast, the methods of this invention allow the breeder to analyze the 1,000 seeds in the lab and select the 50 desired seeds prior to planting. The 50 individuals can then be planted in the field, consuming only two 25 seed rows. Additionally, the methods of this invention do not require tagging or sampling in the field, thereby significantly reducing the required manual labor resources.

In addition to reducing the number of field rows per population, the methods of this invention may further increase the number of populations the breeder can evaluate in a given breeding nursery. Using the above example wherein 50 seeds out of each population of 1000 seeds contained the desired genetic composition, a breeder applying the methods of this invention could evaluate 20 populations of 50 seeds each using the same field area consumed by a single population using conventional field tissue sampling techniques. Even if the populations are selected for a single allele, using a 1:2:1 expected segregation ratio for an $F_2$ population, the breeder could evaluate 4 populations in the same field area as a single field tissue sampled population.

A potential further advantage to the methods of the present invention is the mitigation of risks associated with growing plants in certain geographies where plants may grow poorly or experience poor environmental conditions, or may even be destroyed during storms. For example, seeds with the "best" genotype or marker composition could be planted in geography 1 and seeds with the "next best" genotype could be planted in geography 2. In this case geography 2 would be a backup in case any problem befell the plants grown in geography 1. This is very difficult to do with the traditional method of taking tissue samples from germinated plants for genotyping, because these plants would then need to be uprooted and transplanted to the second geography. Using the methods of this invention avoids the problem of transplantation and also simplifies the logistics of the breeding program.

The methods of the invention may further be used in a breeding program for introgressing a trait into a plant. Such methods comprise removing a sample comprising cells with nucleic acids from seeds in a population, analyzing the nucleic acids extracted from each seed for the presence or absence of at least one genetic marker, selecting seeds from the population based upon the results of the nucleic acids analysis; cultivating a fertile plant from the seed; and utilizing the fertile plant as either a female parent or male parent in a cross with another plant.

Examples of genetic analyses to select seeds for trait integration include, without limitation, identification of high recurrent parent allele frequencies, tracking of transgenes of interest or screening for the absence of unwanted transgenes, selection of hybrid testing seed, selection of seed expressing a gene of interest, selection of seed expressing a heritable phenotype, identification of seed with selected genetic loci, and zygosity testing.

The identification of high recurrent pair allele frequencies via the methods of the present invention again allows for a reduced number of rows per population and an increased number of populations, or inbred lines, to be planted in a given field unit. Thus, the methods of the present invention may also effectively reduce the resources required to complete the conversion of inbred lines.

The methods of the present invention further provide quality assurance (QA) and quality control (QC) by assuring that regulated or unwanted transgenes, undesirable genetic traits, or undesirable inherited phenotypes are identified and discarded prior to planting. This application in a QA capacity could effectively eliminate unintentional release infractions. A further extension of the method is to screen for the presence of infectious agents and remove contaminated seed prior to shipping.

The methods of the present invention may be further applied to identify hybrid seed for transgene testing. For example, in a conversion of an inbred line at the $BCnF_1$ stage, a breeder could effectively create a hybrid seed lot (barring gamete selection) that was 50% hemizygous for the trait of interest and 50% homozygous for the lack of the trait in order to generate hybrid seed for testing. The breeder could then analyze all $F_1$ seeds produced in the test cross and identify and select those seeds that were hemizygous. Such method is advantageous in that inferences from the hybrid trials would represent commercial hybrid genetics with regard to trait zygosity.

Other applications of the methods of this invention for identifying, tracking, and stacking traits of interest carry the same advantages identified above with respect to required field and labor resources. Generally, transgenic conversion programs are executed in multi-season locations which carry a much higher land and management cost structure. As such, the impact of either reducing the row needs per population or increasing the number of populations within a given field unit are significantly more dramatic on a cost basis versus temperate applications.

The methods of this invention may be used for seeds from plants with two or more transgenes, wherein accumulating or stacking of transgenic regions into plants or lines is achieved by addition of transgenes by transformation, or by crossing parent plants or lines containing different transgenic regions, or any combination of these. Analyses can be conducted to select individual seeds on the basis of the presence of one or more characteristics associated with at least one transgene. Such characteristics include, but are not limited to, a transgene per se, a genetic marker linked to a transgene, mRNA expressed from a transgene, and a protein product of a transgene.

Still further, the methods of this invention may be used to improve the efficiency of the doubled haploid program through selection of desired genotypes at the haploid stage and identification of ploidy level to eliminate non-haploid seeds from being processed and advancing to the field. Both applications again result in the reduction of field resources per population and the capability to evaluate a larger number of populations within a given field unit.

Doubled haploid (DH) plants provide an invaluable tool to plant breeders, particularly for generating inbred lines. A great deal of time is spared as homozygous lines are essentially instantly generated, negating the need for multigenerational conventional inbreeding.

In particular, because DH plants are entirely homozygous, they are very amenable to quantitative genetics studies. Both additive variance and additive×additive genetic variances can be estimated from DH populations. Other applications include identification of epistasis and linkage effects. For breeders, DH populations have been particularly useful in QTL mapping, cytoplasmic conversions, and trait introgression. Moreover, there is value in testing and evaluating homozygous lines for plant breeding programs. All of the genetic variance is among progeny in a breeding cross, which improves selection gain.

However, it is well known in the art that DH production process is inefficient and can be quite labor-intensive. While doubled haploid plants can occur spontaneously in nature, this is extremely rare. Most research and breeding applications rely on artificial methods of DH production. The initial step involves the haploidization of the plant which results in the production of a population comprising haploid seed. Non-homozygous lines are crossed with an inducer parent, resulting in the production of haploid seed. Seed that has a haploid embryo, but normal triploid endosperm, advances to the second stage. That is, haploid seed and plants are any plant with a haploid embryo, independent of the ploidy level of the endosperm.

After selecting haploid seeds from the population, the selected seeds undergo chromosome doubling to produce doubled haploid seeds. A spontaneous chromosome doubling in a cell lineage will lead to normal gamete production or the production of unreduced gametes from haploid cell lineages. Application of a chemical compound, such as colchicine, can be used to increase the rate of diploidization. Colchicine binds to tubulin and prevents its polymerization into microtubules, thus arresting mitosis at metaphase, can be used to increase the rate of diploidization, i.e. doubling of the chromosome number These chimeric plants are self-pollinated to produce diploid (doubled haploid) seed. This DH seed is cultivated and subsequently evaluated and used in hybrid testcross production.

However, processes for producing DH seed generally suffer from low efficacy even though methods have been developed in an attempt to increase DH production frequency, including treatment with colchicines. Outstanding issues include low production of haploid seed, reduced gamete viability resulting in diminished self-pollination for DH plant generation, and inadequate DH seed yield for breeding applications.

The methods of the present invention represent an advance in breeding applications by facilitating the potential for selection at the haploid as well as the diploid seed stage. For example, in one embodiment, the invention provides for the high-throughput analysis of a population of haploid seed. The method generally comprises non-destructively removing a sample from a plurality of seeds in the population and analyzing the sample for the presence of one or more characteristics indicative of at least one genetic or chemical trait as described herein.

In another embodiment, the invention provides for the high-throughput bulking of a population of doubled haploid seeds. The method comprises selecting one or more individual seeds exhibiting at least one preferred characteristic from a population of haploid seeds and producing a population of doubled haploid seeds from the selected seeds. Each doubled haploid seed is then non-destructively sampled and the samples are analyzed for the presence or absence of one or more characteristics indicative of at least one genetic or chemical trait. Based on the results of the analysis, one or more individual doubled haploid seeds are selected and plants or plant tissue is cultivated from the selected doubled haploid seeds.

In various embodiments, the methods of the invention include analyzing seed for one or more characteristics, such as genetic markers, to determine whether the seed is in a haploid or diploid state. The present invention also provides a methods for analyzing haploid and doubled haploid seed for one or more characteristics, such as transgenes or markers linked to or diagnostic of transgenes, for characteristics related to event performance, event evaluation, and trait integration. Further, the present invention provides a method to assay haploid seed in order to select preferred genotypic and phenotypic classes to undergo doubling.

In another embodiment, the present invention provides a basis for determination of linkage phase. By using seed endosperm tissue derived from a diploid plant, the parental marker haplotypes can be determined using a genotyping system that enables detection of different allele frequencies in DNA samples. Since endosperm tissue is triploid, with two copies derived from the female gamete, the linkage phase of the parental line can be derived by dissecting heterozygous progeny genotypes (see FIG. 1). The DNA sample from endosperm tissue allows for a determination of the ploidy level of the genetic marker. A diploid ploidy level in the genetic marker indicates maternal inheritance and a haploid ploidy level in the genetic marker indicates paternal inheritance.

Further, differential allele frequency data can be used to infer the genetic linkage map but, unlike methods requiring haploid material (Gasbarra et al. 2006 Genetics 172:1325-1335), using the above-described allele frequency calling. Determination of the genetic linkage map has tremendous utility in the context of haplotype characterization, mapping of marker (or haplotype)—trait associations. This method is particularly robust on a single, vs. bulked, seed basis and is thus well-suited to the present invention.

In a particular embodiment, the invention further provides an assay for predicting embryo zygosity for a particular gene of interest (GOI). The assay predicts embryo zygosity based on the ratio of the relative copy numbers of a GOI and of an internal control (IC) gene per cell or per genome. Generally, this assay uses an IC gene that is of known zygosity, e.g., homozygous at the locus (two IC copies per diploid cell), for normalizing measurement of the GOI. The ratio of the relative copy numbers of the IC to the GOI predicts the GOI copy number in the cell. In a homozygous cell, for any given gene (or unique genetic sequence), the gene copy number is equal to the cell's ploidy level since the sequence is present at the same locus in all homologous chromosomes. When a cell is heterozygous for a particular gene (or hemizygous in the case of a transgene), the gene copy number will be lower than the cell's ploidy level. If the GOI is not detected, the cell is null for the locus, as can happen for a negative segregant of a transgenic event or in a mutagenized population. The zygosity of a cell at any locus can thus be determined by the gene copy number in the cell.

In another particular embodiment, the invention provides an assay for predicting corn embryo zygosity. In corn seed, the endosperm tissue is triploid, whereas the embryo tissue is diploid. Endosperm copy number is reflective of the zygosity of the embryo: a homozygous (positive or negative) endosperm accompanies a homozygous embryo, heterozygous endosperm (whether a GOI copy number of 1 or 2) reflects a heterozygous (GOI copy number of 1) embryo. Endosperm that is homozygous for the IC will contain three IC copies. Endosperm GOI copy number can range from 0

(homozygous negative embryo) to 3 (homozygous positive embryo); and endosperm GOI copy number of 1 or 2 is found in seed where the embryo is heterozygous for the GOI (or hemizygous for the GOI if the GOI is a transgene). The endosperm GOI copy number (which can range from 0 to 3 copies) can be determined from the ratio of endosperm IC copy number to endosperm GOI copy number (which can range from 0/3 to 3/3, that is, from 0 to 1), which can then be used to predict zygosity of the embryo.

Copy numbers of the GOI or of the IC can be determined by any convenient assay technique for quantification of copy numbers, as is known in the art. Examples of suitable assays include, but are not limited to, Real Time (TaqMan®) PCR (Applied Biosystems, Foster City, Calif.) and Invader® (Third Wave Technologies, Madison, Wis.) assays. Preferably, such assays are developed in such a way that the amplification efficiency of both the IC and GOI sequences are equal or very similar. For example, in a Real Time TaqMan® PCR assay, the signal from a single-copy GOI (the source cell is determined to be heterozygous for the GOI) will be detected one amplification cycle later than the signal from a two-copy IC, because the amount of the GOI is half that of the IC. For the same heterozygous sample, an Invader® assay would measure a GOI/IC ratio of about 1:2 or 0.5. For a sample that is homozygous for both the GOI and the IC, the GOI signal would be detected at the same time as the IC signal (TaqMan®), and the Invader assay would measure a GOI/IC ratio of about 2:2 or 1.

These guidelines apply to any polyploid cell, or to haploid cells (such as pollen cells), since the copy number of the GOI or of the IC remain proportional to the genome copy number (or ploidy level) of the cell. Thus, these zygosity assays can be performed on triploid tissues such as corn endosperm. Furthermore, the copy number for a GOI can be measured beyond 2 copies or at numerically different values than the ploidy of the cell. The method is still appropriate for detecting GOI in polyploids, in some transgenic events with >2 copies of the inserted transgene, after replication of the GOI by transposition, when the GOI exists on autonomously replicating chromosomes or plasmids and other situations.

In plant breeding, it is useful to determine zygosity at one or more loci for the purpose of evaluating the level of inbreeding (that is, the degree of gene fixation), segregation distortion (i.e., in transgenic germplasm, maternal inheritance testing or for loci that affect the fitness of gametes), and the level of outbreeding (i.e., the relative proportion of homozygosity and heterozygosity). Similarly, the extent of zygosity at one or more loci can be used to estimate hybridity and whether a particular seed lot meets a commercial or regulatory standard for sale as certified hybrid seed. In addition, in transgenic germplasm, it is useful to know the ploidy, or copy number, in order to distinguish between quality events and to aid in trait integration strategies.

In another embodiment, the present invention provides a basis for improving the ability to monitor one or more germplasm pools for shifts in the frequencies of one or more genetic characteristics, wherein said genetic characteristics include markers, alleles, and haplotypes. Methodology is known in the art to compare genetic marker frequency between recently derived populations and their ancestral lines in order to identify those genetic loci that are increasing in frequency over time (U.S. Pat. Nos. 5,437,697 and 5,746,023). Those loci with frequencies that exceed the expected allele frequency are inferred to have been subject to selection. Further, given that the predominant selection criterion in breeding programs is yield, it is expected that those increasingly frequent alleles may be linked to yield.

In a particular embodiment, the present invention provides a method to enable haplotype-assisted breeding. By comparing the frequency of haplotypes in emerging elite lines with the haplotype frequency in the ancestral elite lines (as determined via pedigree analysis), identification of haplotypes that are deviating from the expected haplotype frequency is possible. Further, by evaluation of haplotype effect estimates for said haplotypes, it is also possible to link said haplotypes of increasing frequency with phenotypic outcomes for a suite of agronomic traits. The haplotype composition of individual seeds sampled from a plurality of seeds can be determined using genetic markers and the seeds with preferred haplotypes are selected and advanced. Thus, more informed breeding decisions and establishment of superior line development programs is enabled by this technology.

EXAMPLES

The following examples are merely illustrative, and not limiting to this disclosure in any way.

Example 1

This example describes an assay for predicting the zygosity of corn embryos using an internal control (IC) gene homozygous at the locus (i.e., two IC copies in the diploid embryo and three IC copies in the triploid endosperm). In an inbred line of a diploid (or higher ploidy) organism such as corn, the endogenous internal control is typically homozygous; transgenic events in such organisms at the first generation (termed "R0" in corn) are typically hemizygous (that is, the transgene is typically present in only one of the two or more homologous chromosomes). Corn (*Zea mays*) is a diploid organism, thus a "single copy" R0 event has one copy of the GOI per cell, but 0.5 copies per haploid genome, a "two copy" R0 event has two copies of the GOI per cell, but 1 copy per haploid genome, and so forth.

In this example, tubulin was used as the IC gene, and the GOI was a transgene encoding neomycin phosphotransferase II (NPT II), which is used for kanamycin resistance selection. Endosperm (triploid) tissue was taken from seed (either by hand sampling or by scraping a seed with an automated sampler of the present invention). The endosperm-sampled seed was germinated, and leaf tissue (diploid) from successfully germinated plants was also sampled for genetic analysis. The leaf tissue correlates directly with embryo zygosity and was thus used to demonstrate that endosperm zygosity generally predicted zygosity of the embryo and to confirm homozygosity calls from the endosperm. Total genomic DNA was extracted from endosperm tissue and from leaf tissue, and quantitatively analyzed using an Invader® assay with oligonucleotide probes specific for the gene of interest, NPT II, or for the internal control gene, tubulin. The ratio of the GOI to IC was measured using conventional molecular biology techniques. See Table 1. A summary of results of multiple experiments are shown in Table 2.

Results indicated that endosperm zygosity generally predicted zygosity of the embryo (as indicated by the leaf zygosity) and was reliable in predicting homozygosity for all seeds that germinated. Furthermore, endosperm zygosity analysis gave few false-negative homozygous predictions (especially when the endosperm tissue was obtained with the automated sampler). These results demonstrate that for a cell of a known ploidy level, the ratio of copy number of a GOI to that of an IC indicates the zygosity of that cell. Furthermore, the zygosity assay of the present invention can predict zygosity of one tissue based on the zygosity of another, that is, the assay can predict the embryo zygosity based on the endosperm zygosity.

TABLE 1

| Automated Ratio | Automated Zygosity | Manual Ratio | Manual Zygosity |
|---|---|---|---|
| 1.39 | Heterozygous | 1.42 | Heterozygous |
| 0.14 | neg homozygous | 0.12 | neg homozygous |
| 0.08 | neg homozygous | 0.08 | neg homozygous |
| 0.13 | neg homozygous | 0.10 | neg homozygous |
| 0.10 | neg homozygous | 0.08 | neg homozygous |
| 1.55 | Heterozygous | 1.38 | Heterozygous |
| 0.84 | Heterozygous | 1.45 | Heterozygous |
| 0.14 | neg homozygous | 1.48 | Heterozygous |
| 1.48 | Heterozygous | 1.37 | Heterozygous |
| 1.39 | Heterozygous | 1.47 | Heterozygous |
| 2.03 | POS homozygous | 1.93 | POS homozygous |
| 0.13 | neg homozygous | 0.05 | neg homozygous |
| 1.71 | Inconclusive | 1.81 | POS homozygous |
| 0.81 | Heterozygous | 1.41 | Heterozygous |
| 1.84 | POS homozygous | 1.77 | POS homozygous |
| 1.54 | Heterozygous | 1.43 | Heterozygous |
| 1.48 | Heterozygous | 1.50 | Heterozygous |
| 0.92 | Heterozygous | 1.40 | Heterozygous |
| 1.51 | Heterozygous | 1.42 | Heterozygous |
| 1.60 | Heterozygous | 1.37 | Heterozygous |
| 0.86 | Heterozygous | 1.47 | Heterozygous |
| 1.81 | POS homozygous | 2.02 | POS homozygous |
| 0.15 | neg homozygous | Low DNA | |
| 1.89 | POS homozygous | 1.85 | POS homozygous |
| 0.21 | neg homozygous | 0.10 | neg homozygous |
| 0.09 | neg homozygous | 0.11 | neg homozygous |
| 0.89 | Heterozygous | 1.50 | Heterozygous |
| 1.50 | Heterozygous | 1.37 | Heterozygous |
| 1.82 | Inconclusive | 2.02 | POS homozygous |
| 2.14 | POS homozygous | 0.99 | inconclusive |
| 1.22 | Heterozygous | 1.44 | Heterozygous |
| 2.22 | POS homozygous | 2.24 | POS homozygous |
| 0.79 | Heterozygous | 1.40 | Heterozygous |
| 1.23 | Heterozygous | 1.47 | Heterozygous |
| 1.49 | Heterozygous | 1.38 | Heterozygous |
| 1.33 | Heterozygous | 1.37 | Heterozygous |

TABLE 2

| Endosperm sampling method | Number of homozygous seeds identified by endosperm analysis | Number of predicted homozygous seeds that did not germinate | Number of confirmed homozygous calls based on leaf analysis | Number of false negative homozygous calls based on endosperm analysis |
|---|---|---|---|---|
| Hand | 8 out of 36 | 0 | 8 (all) | 5 (13.9%) |
| Automated | 6 out of 24 | 1 | 5 | 0 |
| Hand | 6 out of 36 | 0 | 6 (all) | 2 (5.6%) |
| Automated | 6 out of 24 | 1 | 5 | 0 |
| Hand | 5 out of 36 | 0 | 5 (all) | 7 (19.4%) |
| Automated | 7 out of 24 | 2 | 5 | 0 |
| Hand | 7 out of 36 | 1 | 6 | 0 |
| Automated | 5 out of 24 | 2 | 3 | 0 |

Example 2

This example demonstrates the use of the methods of the present invention in a program for marker-assisted selection of soybeans for Low Linolenic Acid.

Soybean is the most valuable legume crop, with many nutritional and industrial uses due to its unique chemical composition. Soybean seeds are an important source of vegetable oil, which is used in food products throughout the world. The relatively high level (usually about 8%) of linolenic acid (18:3) in soybean oil reduces its stability and flavor. Hydrogenation of soybean oil is used to lower the level of linolenic acid (18:3) and improve both stability and flavor of soybean oils. However, hydrogenation results in the production of trans fatty acids, which increases the risk for coronary heart disease when consumed. The development of low linolenic acid soybean has been complicated by the quantitative nature of the trait. The low linolenic acid soybean varieties that have been developed have been found to yield poorly, limiting their usefulness in most commercial settings. Developing a product with commercially significance seed yield is a high priority in most soybean cultivar development programs.

An example of the application of the methods of the present invention is selection of soybean plants with both high yield and decreased linolenic acid content. Soybean progeny performance as it relates to low linolenic acid relies mainly on two major quantitative trait locus (QTL) at Fad3-1b and Fad3-1c. Analysis of segregating plants demonstrated that Fad3-1b and Fad3-1c additively control linolenic content in soybean. Therefore, by using a combination of markers for Fad3-1b and Fad3-1c, a breeder using the invention can accurately predict linolenic acid content in soybean plants. The markers can be used to infer the genotypic state of a seed at any stage in the breeding process, for example, at the finished inbred line stage, or the $F_1$, $F_2$, $F_3$, etc.

A seminal $F_1$ hybrid can be produced by crossing two inbred soybean lines (for example, crossing a plant containing the Fad3-1b and/or Fad3-1c alleles associated with decreased linolenic acid content to a plant lacking these alleles) followed by natural self-pollination. Since the markers can be used to infer the genotypic state of a single seed obtained from an intermating of such inbred lines, early generation (i.e., $F_2$) marker-assisted breeding can be conducted.

Soybean seed at ambient temperature and humidity typically equilibrate to 8% moisture on a dry weight basis. Soybean seed at this level of moisture tends to split when sampled. To reduce splitting, seed should be humidified to moisture level of 12%. When pretreated in this manner, splitting is significantly reduced to <5%.

The selected $F_2$ seed that have the desired genotype may be bulked or kept separate depending on the breeding objectives. If multiple QTL with varying effects were being selected from a given population, the breeder could preserve single seed identity to differentiate individuals with various combinations of the target resistance QTL. These seeds could be planted in the field with appropriate field identification. Several methods of preserving single seed identity can be used while transferring seed from the sampling lab to the field. Methods include transferring selected individuals to horticultural seed tape that could also include radio frequency identification to aid in the identification of the individual genotyped seed. Other methods would be to use an indexing tray, plant seeds in peat pots and then transplant them, or hand plant from individual seed packets.

Example 3

This example demonstrates the use of the methods of the present invention in a program for recurrent parent alleles in a backcross breeding program.

The methods of the present invention can be used for selection of transgenes as well as identification of recurrent parent alleles. The identification of genotypes with desired recurrent parent allele frequencies before planting allows the number of rows per population to be reduced throughout the entire breeding program along with an increase in the number of populations included in the conversion program within a given field unit. This results in improved land usage, reduced land and labor costs, etc.

An example of analyzing endosperm tissue from corn for recurrent parent alleles in a backcross breeding program is shown in FIG. 1.

Example 4

This example demonstrates the use of the methods of the present invention for use in DNA line fingerprinting and linkage phase determination.

Combined with bulking of a single seed's DNA, line fingerprinting could be accomplished without the need to sample the line in the field.

By using seed endosperm tissue (seed coat in soybean) derived from a diploid plant, the parental marker haplotypes can be determined using a genotyping system that enables detection of different allele frequencies in DNA samples. Since endosperm tissue is triploid, with two copies derived from the female gamete, the linkage phase of the parental line can be derived by dissecting heterozygous progeny genotypes. The DNA sample from endosperm tissue allows for a determination of the ploidy level of the genetic marker. A diploid ploidy level in the genetic marker indicates maternal inheritance and a haploid ploidy level in the genetic marker indicates paternal inheritance.

Example 5

This example demonstrates the methods of the present invention for evaluating transgenic seed for segregation distortion. Seeds of an F1 cross between Line A (Homozygous Event 1 and Event 2) and Line B (Homozygous Event 1) were induced in a maternal haploid induction isolation. The resulting kernels were selected using plumule color to obtain a population of putative haploid seed.

Individual putative haploid kernels from the population of putative haploid seed were selected and non-destructively sampled using an automated seed sampler system as generally described in U.S. patent application Ser. No. 11/213,435 (Publication No. US 2006/004624), which is hereby incorporated by reference in its entirety. Markers were applied to the samples to determine the presence of the Event 2 gene and the Event 1 gene. The sampling process clips off some pericarp and endosperm tissue and uses this as the base for analysis. It is important to note that endosperm tissue is triploid and contains genetic contribution from both parents. If the gene of interest is detected using this method, it accurately predicts the presence of the desired gene in the haploid embryo. For the purposes of this study, samples from 180 kernels were analyzed and data were obtained on 175 due to sampling issues.

As shown in Table 3 below, each of the seed samples tested positive for the Event 1 gene as expected and approximately 50% of the seed samples tested positive for the Event 2 gene, confirming no segregation distortion.

TABLE 3

|  | Event 2 | Event 1 |
|---|---|---|
| Pedigree |  |  |
| Chromosome | 6 | 8 |
| Position | 38 | 63 |

TABLE 3-continued

|  | Event 2 | Event 1 |
|---|---|---|
| Parental Checks |  |  |
| Line A | Pos | Pos |
| Line B | Neg | Pos |
| KHI1 | Neg | Neg |
| Selected Kernels | 175 | 175 |
| Total Positive | 92/175 | 175/175 |
| Total Negative | 83/175 | 0/175 |

Results of this study indicate that individual gene traits can be selected on a haploid basis using high throughput, nondestructive seed sampling as a screening mechanism.

Example 6

This example demonstrates the utility of automated, high-throughput sampling in the preselection of haploid seed from a population of seeds.

The experiment comprised sampling 20 F2 populations using a nondestructive, high throughput seed sampling system and analyzing the samples to verify the pre-selection of haploid seed. Each population of F2 seed was nondestructively sampled or the F2 plants were tissue sampled for DNA analysis. The nondestructive seed samples were collected from individual seeds in the population of seeds using an automated seed sampler system as generally described in U.S. patent application Ser. No. 11/213,435 (Publication No. US 2006/004624), which is hereby incorporated by reference in its entirety. Selection of desirable genotypes was based on selecting materials with the greatest allelic frequencies of the desired haplotypes based on modeling parameters. The selected F2 plants were pollinated with haploid inducing male pollinators and the resulting seed is harvested. Following harvest, haploid kernels were sorted out from the non-haploid seed and the haploids were sampled on a kernel basis using nondestructive, high throughput sampling and subsequent genotyping. The preferred haploid seed was selected and subjected to a chromosome doubling procedure to produce doubled haploids. This approach allows non-preferred genotypes to be culled before doubling and increases the frequency of preferred material that is processed through the resource intensive doubling process.

Figure 2:
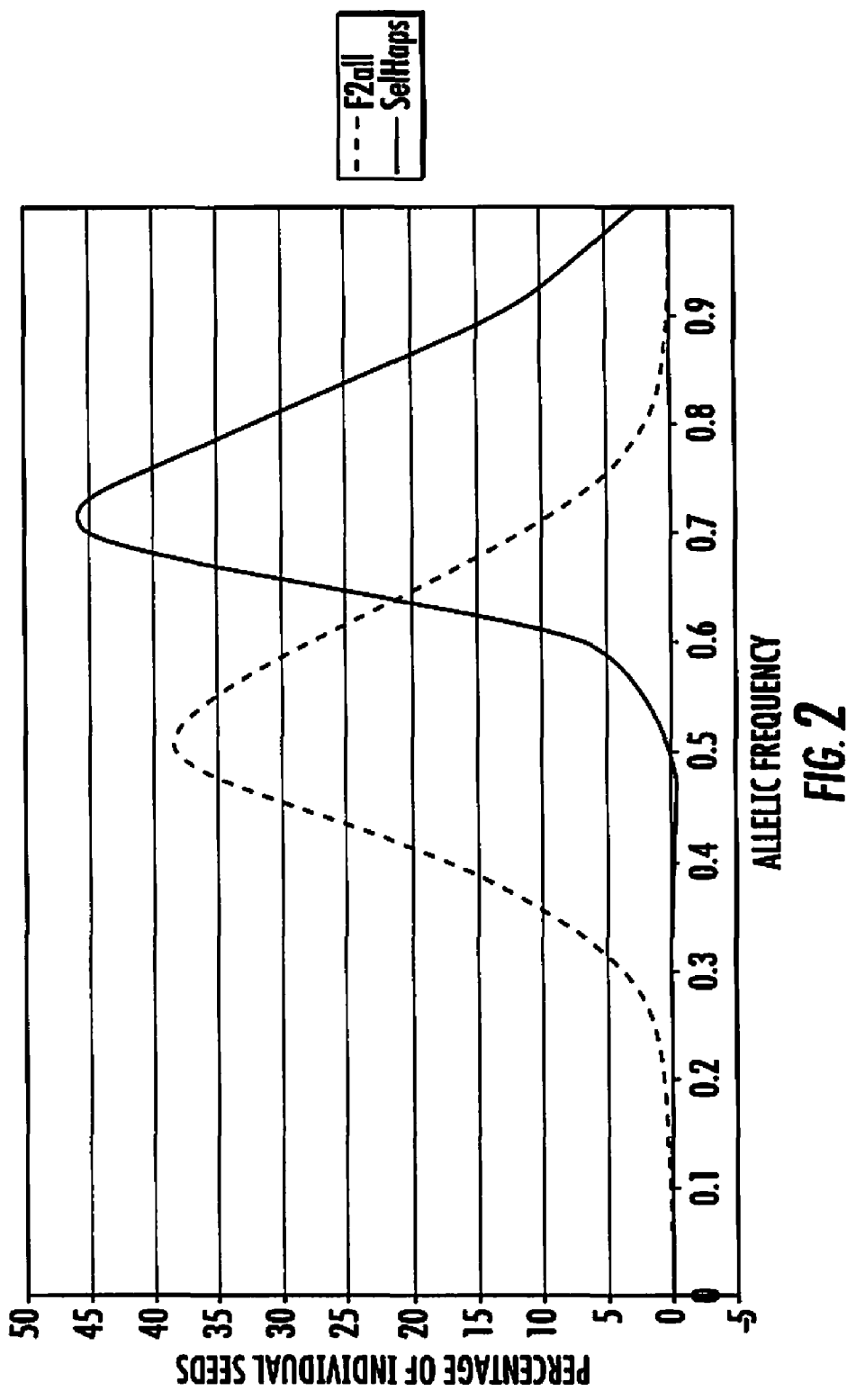
FIG. 2 is a graphical illustration of the efficacy of pre-selection on driving the frequency of favorable haplotypes as described in Example 6.

Results comparing the selected haploid seed and illustrating the efficacy of this approach are shown in FIG. 2.

When introducing elements or features of embodiments herein, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

The description of the disclosure is merely exemplary in nature and, thus, variations that do not depart from the gist of the disclosure are intended to be within the scope of the disclosure. Such variations are not to be regarded as a departure from the spirit and scope of the disclosure.

What is claimed is:

1. A method for analyzing a population of haploid seeds, the method comprising:
   removing tissue from individual seeds in a population of haploid seeds using an automated seed sampler system while preserving germination viability of the seeds; and
   analyzing the removed tissue for the presence or absence of one or more traits of interest.

2. The method of claim 1, further comprising determining the genotypic character of the seeds in the population.

3. The method of claim 1, further comprising:
   selecting one or more seeds from the population exhibiting the presence or absence of the one or more traits of interest; and
   producing doubled haploid seeds from the selected one or more seeds.

4. The method of claim 3, wherein the one or more traits of interest include a phenotypic characteristic.

5. The method of claim 1, wherein the one or more traits of interest are selected from the group consisting of a genetic marker, a single nucleotide polymorphism, a simple sequence repeat, a restriction fragment length polymorphism, a haplotype, a tag SNP, an alleles of a genetic marker, a gene, a DNA-derived sequence, an RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation pattern.

6. The method of claim 1, further comprising selecting one or more seeds from the population of seeds based on the presence or absence of the one or more traits of interest; and wherein the one or more traits of interest include one or more transgenes.

7. The method of claim 1, wherein the one or more traits of interest include one or more undesirable genetic characteristics; the method further comprising selecting one or more seeds from the population of seeds based on the presence or absence of the one or more undesirable genetic characteristics, and discarding the selected seeds.

8. The method of claim 1, wherein the one or more traits of interest include one or more chemical traits.

9. The method of claim 8, wherein the one or more traits of interest are selected from the group consisting of proteins, oils, carbohydrates, fatty acids, amino acids, biopolymers, pharmaceuticals, starch, fermentable starch, secondary compounds, and metabolites.

10. The method of claim 1, wherein the one or more traits of interest include one or more genetic traits.

11. The method of claim 1, further comprising selecting one or more seeds from the population of seeds based on the presence or absence of the one or more traits of interest; and wherein the one or more traits of interest are genetically linked with a QTL selected from the group consisting of herbicide tolerance, disease resistance, insect or pest resistance, altered fatty acid, protein or carbohydrate metabolism, increased grain yield, increased oil, increased nutritional content, increased growth rates, enhanced stress tolerance, preferred maturity, enhanced organoleptic properties, altered morphological characteristics, other agronomic traits, traits for industrial uses, traits for improved consumer appeal, and a combination of traits as a multiple trait index.

12. The method of claim 1, further comprising selecting one or more seeds from the population of seeds based on the presence or absence of the one or more traits of interest; and wherein the one or more traits of interest are genetically linked with a haplotype associated with a QTL selected from the group consisting of herbicide tolerance, disease resistance, insect or pest resistance, altered fatty acid, protein or carbohydrate metabolism, increased grain yield, increased oil, increased nutritional content, increased growth rates, enhanced stress tolerance, preferred maturity, enhanced organoleptic properties, altered morphological characteristics, other agronomic traits, traits for industrial uses, traits for improved consumer appeal, and a combination of traits as a multiple trait index.

13. The method of claim 1, further comprising selecting one or more seeds from the population of seeds based on the presence or absence of the one or more traits of interest; and wherein the one or more traits of interest are indicative of association with a recurrent parent to facilitate selection for marker-assisted backcrossing.

14. The method of claim 1, further comprising:
   quantifying one or more characteristics from the removed tissue; and
   comparing the quantified characteristics to characteristics of two or more known germplasm pools to identify frequency shifts.

15. The method of claim 14, wherein the two or more germplasm pools represent a crop selected from the group consisting of a forage crop, oilseed crop, grain crop, fruit crop, ornamental plants, vegetable crop, fiber crop, spice crop, nut crop, turf crop, sugar crop, beverage crop, tuber crop, root crop, and forest crop.

16. The method of claim 1, further comprising removing the tissue from an endosperm portion of the seeds.

17. The method of claim 16, further comprising:
   analyzing the removed tissue for one or more alleles; and
   determining a ploidy level of at least one locus.

18. The method of claim 17, wherein the ploidy level is determined by analyzing the removed tissue for an allele derived from maternal parents of the seeds.

19. The method of claim 17, wherein the ploidy level is determined by analyzing the removed tissue for an allele derived from paternal parents of the seeds.

20. The method of claim 1, further comprising selecting one or more seeds from the population of seeds based on the presence or absence of the one or more traits of interest, and cultivating plants or plant tissue from the selected seeds.

21. The method of claim 20, further comprising coating the one or more selected seeds with a polymer and/or a fungicide after removing the tissue therefrom to further preserve germination viability.

22. The method of claim 20, further comprising determining the genotypic character of the seed's offspring prior to selecting seeds from the population.

23. The method of claim 20, further comprising using fertile plants cultivated from the selected seeds as either female or male parents in a cross with another plant.

24. The method of claim 1, further comprising pre-sorting the population of haploid seeds based on the presence or absence of a physical and/or morphological trait.

25. The method of claim 1, wherein the population of haploid seeds comprises seeds selected from the group consisting of alfalfa seed, apple seed, banana seed, barley seed, bean seed, broccoli seed, castorbean seed, citrus seed, clover seed, coconut seed, coffee seed, maize seed, cotton seed, cucumber seed, Douglas fir seed, Eucalyptus seed, Loblolly pine seed, linseed seed, melon seed, oat seed, olive seed, palm seed, pea seed, peanut seed, pepper seed, poplar seed, Radiata pine seed, rapeseed seed, rice seed, rye seed, sorghum seed, Southern pine seed, soybean seed, strawberry seed, sugarbeet seed, sugarcane seed, sunflower seed, sweetgum seed, tea seed, tobacco seed, tomato seed, turf seed, wheat seed, and *Arabidopsis thaliana* seed.

26. The method of claim 1, wherein the one or more traits of interest include physical, morphological, chemical, and/or genetic traits.

* * * * *